(12) United States Patent
Banov

(10) Patent No.: US 9,931,366 B2
(45) Date of Patent: Apr. 3, 2018

(54) TOPICAL PHARMACEUTICAL BASES FOR WOUND AND SCAR TREATMENT

(71) Applicant: Professional Compounding Centers of America (PCCA), Houston, TX (US)

(72) Inventor: Daniel Banov, Sugar Land, TX (US)

(73) Assignee: Professional Compounding Centers of America, Houston, TX (US)

( * ) Notice: Subject to any disclaimer, the term of this patent is extended or adjusted under 35 U.S.C. 154(b) by 172 days.

(21) Appl. No.: 14/831,621

(22) Filed: Aug. 20, 2015

(65) Prior Publication Data

US 2016/0051611 A1 Feb. 25, 2016

Related U.S. Application Data

(60) Provisional application No. 62/039,797, filed on Aug. 20, 2014.

(51) Int. Cl.

| | |
|---|---|
| *A61K 36/58* | (2006.01) |
| *A61K 36/49* | (2006.01) |
| *A61K 36/185* | (2006.01) |
| *A61K 45/06* | (2006.01) |
| *A61K 9/00* | (2006.01) |
| *A61L 15/40* | (2006.01) |
| *A61L 26/00* | (2006.01) |

(52) U.S. Cl.
CPC ............ *A61K 36/58* (2013.01); *A61K 9/0014* (2013.01); *A61K 36/185* (2013.01); *A61K 36/49* (2013.01); *A61K 45/06* (2013.01); *A61L 15/40* (2013.01); *A61L 26/0057* (2013.01)

(58) Field of Classification Search
CPC ...................................................... A61K 36/00
See application file for complete search history.

(56) References Cited

U.S. PATENT DOCUMENTS

2009/0285876 A1* 11/2009 Hein ...................... A61K 8/375
424/443

* cited by examiner

*Primary Examiner* — Qiuwen Mi
(74) *Attorney, Agent, or Firm* — David G. Woodral; Scott R. Zingerman; Gable Gotwals

(57) ABSTRACT

The present disclosure refers to topical pharmaceutical bases that include a synergistic combination of pracaxi oil, andiroba oil, copaiba balsam, and ucuuba butter. Further, these topical pharmaceutical bases are proposed for treating skin conditions in mammals, such as, for example wounds and scars. The topical pharmaceutical bases provide healing, moisturizing, anti-inflammatory, antibacterial, and antifungal effect. Additionally, the topical pharmaceutical bases enable an effective administration of specific active pharmaceutical ingredients (APIs), thereby improving treatment outcomes. Topical pharmaceutical compositions including the topical pharmaceutical bases increase the residence time of APIs within a wound or scar, thereby improving the penetration of APIs into the affected area. Also, the topical pharmaceutical bases provide relatively uniform distribution of the APIs within the topical pharmaceutical compositions. Further, the topical pharmaceutical compositions release APIs slowly, thereby enhancing treatment effectiveness.

4 Claims, No Drawings

TOPICAL PHARMACEUTICAL BASES FOR WOUND AND SCAR TREATMENT

CROSS-REFERENCE TO RELATED APPLICATIONS

This application claims priority to U.S. Provisional Application Ser. No. 62/039,797, filed Aug. 20, 2014, which is hereby incorporated by reference herein.

BACKGROUND

Field of the Disclosure

The present disclosure relates generally to pharmaceutical compositions, and more particularly, to topical pharmaceutical bases including natural components for treating skin conditions.

Background Information

Typically, a healed wound produces a scar. A scar is growth of collagen beneath the skin that is formed as the result of wound healing; therefore, every cut or injury to the skin heals to form a scar. Proper wound healing results in an invisible scar. Early in the process, scars are red or dark and raised, but become paler and flatter over time. While a visible scar is the necessary and inevitable end to the healing process, the results vary with the individual, the type of injury, and time, among others. For example, when scars are over about two months old to about two years old, scars tend to become harder to treat, and after two years a surgery is necessary to remove the scars, which result in new scars appearing after the removal surgery.

Additionally, excessive scarring results from an imbalance in the anabolic and catabolic wound healing processes. In the formation of an abnormal scar, more collagen is produced than is degraded. Therefore, the scar grows larger than is required for wound healing, with an over-production of cells, collagen, and proteoglycan. Scars resulting from excessive scarring or the abnormalities in wound healing include fibrosis, fibromatosis, keloidosis, adhesions (e.g., surgical adhesions), hypertrophic scars, fibrocystic conditions, and joint stiffness. For example, keloids grow in all directions, become elevated above the skin, and remain hyperemic. The exact mechanisms of excessive scarring are poorly understood, but it is believed that common mechanisms underlie the formation of both keloids and hypertrophic scars. Further, research results suggest that increased transforming growth factor β (TGF-β) expression plays a role in excessive scarring, due to promoting extracellular matrix production, and because of being produced at elevated levels by keloid fibroblasts and hypertrophic scars. Abnormal scars or abnormalities in wound healing are also categorized into various conditions based on the type of tissue in which a wound occurs. Abnormal scar formation in skin may lead to, for example, keloid, hypertrophic scar, contracture, or scleroderma.

Generally, methods for treating scars and keloids have a low success probability and are costly and complicated. For example, treatment of keloids and hypertrophic scars has included surgical excision followed by graft application, with a risk of new scars being developed after the excisions. Pressure has also been used to cause scar thinning; for example, pressure bandages placed over scars have resulted in some scar thinning, but a pressure of at least 25 mm Hg needs to be maintained constantly for approximately six months in usual situations for any visually observable effect. Ionizing radiation therapy has also been employed. Other treatments include application of silicone pads to the scar tissue surface, sometimes under pressure provided by an elastomeric bandage; topical application of silicone gel sheets, with or without added vitamin E; and topical or intra-lesional treatment with corticosteroids.

Accordingly, there is a need for pharmaceutical formulations to treat skin conditions that improve wound and scar healing process.

SUMMARY

The present disclosure refers to topical pharmaceutical bases that include a synergistic combination of pracaxi oil, andiroba oil, copaiba balsam, and ucuuba butter. Further, aforementioned components possess significant healing properties, and employed together improve the effectiveness of the wound healing process, as well as the treatment of scars. In some embodiments, the topical pharmaceutical bases provide healing, moisturizing, anti-inflammatory, anti-bacterial, and antifungal effect.

In an example, the topical pharmaceutical bases include a synergistic combination of: pracaxi oil in a concentration from about 5% w/w to 50% w/w; andiroba oil in a concentration from about 5% w/w to 50% w/w; copaiba balsam in a concentration from about 5% w/w to 50% w/w; and ucuuba butter in a concentration from about 5% w/w to 50% w/w.

In other embodiments, the natural topical bases include one or more natural components, such as, for example buriti oil, bacaba oil, acai oil, ojon oil, murumuru butter, and/or tucuma oil, among others. In these embodiments, the concentration of each natural component within the topical pharmaceutical bases is from about 1% w/w to 20% w/w, preferably about 5% w/w.

In further embodiments, the topical pharmaceutical bases enable an effective administration of specific active pharmaceutical ingredients (APIs), thereby improving treatment outcomes. In these embodiments, the topical pharmaceutical bases include suitable APIs, such as, for example antibiotic, antifungal, corticosteroids, non-steroidal anti-inflammatories, antibacterials, antivirals, and analgesics, among others. Further to these embodiments, aforementioned non-steroidal anti-inflammatory drugs include diclofenac, ketoprofen, ibuprofen, and naproxen, among others. In other embodiments, the topical pharmaceutical bases include tamoxifem, metaxalone, and tranilast, among others.

In some embodiments, the topical pharmaceutical bases are directly administered onto the affected area, in a dosage that varies according to the size or weight of the patient. In these embodiments, a single dose is enough to observe healing within the next 7 days after administration.

In some embodiments, topical pharmaceutical compositions including the topical pharmaceutical bases increase the residence time of APIs within a wound or scar, thereby improving the penetration of APIs into the affected area. In these embodiments, the topical pharmaceutical bases provide relatively uniform distribution of the APIs within the topical pharmaceutical compositions. Further to these embodiments, the topical pharmaceutical compositions release APIs slowly, thereby enhancing treatment effectiveness.

Numerous other aspects, features and benefits of the present disclosure may be made apparent from the following detailed description.

DETAILED DESCRIPTION

The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

Definitions

As used here, the following terms have the following definitions:

"Active Pharmaceutical Ingredients (APIs)" refer to chemical compounds that induce a desired effect, and include agents that are therapeutically effective, prophylactically effective, or cosmeceutically effective.

"Balsam" refers to oily or viscous oleoresins, usually having benzoic or cinnamic acid.

"Butter" refers to a moisturizing product obtained of oils extracted from seeds and nuts. Butters are solid at room temperature, but melt on the skin.

"Oil" refers to a vegetable substance that may be clear, odorless, viscous, hydrophobic, liquid or liquefiable at room temperature. Oils are widely used in cosmetics due to its hypoallergenic and noncomedogenic properties.

"Treating" and "Treatment" refers to reduction in severity and/or frequency of symptoms, elimination of symptoms and/or underlying cause, prevention of the occurrence of symptoms and/or their underlying cause, and improvement or remediation of damage.

Description of the Disclosure

The present disclosure refers to topical pharmaceutical bases that include a synergistic combination of pracaxi oil, andiroba oil, copaiba balsam, and ucuuba butter. Further, these topical pharmaceutical bases are proposed for treating skin conditions in mammals, such as, for example wounds, scars, and the like.

In some embodiments, the topical pharmaceutical bases provide healing, moisturizing, anti-inflammatory, antibacterial, and antifungal effect. In these embodiments, the topical pharmaceutical bases include one or more naturally occurring substances, including one or more oils rich in essential fatty acids. Further to these embodiments, the topical pharmaceutical bases include oils having properties that increase wound healing process, thereby enabling treatment of scars.

Formulation

In some embodiments, the topical pharmaceutical bases include natural components from the Amazon forest. In these embodiments, topical pharmaceutical bases include a synergistic combination of pracaxi oil, andiroba oil, copaiba balsam, and ucuuba butter. Further to these embodiments, the natural components exhibit moisturizing, antimicrobial, and healing properties.

In an example, the topical pharmaceutical bases include a synergistic combination of: pracaxi oil in a concentration from about 5% w/w to 50% w/w; andiroba oil in a concentration from about 5% w/w to 50% w/w; copaiba balsam in a concentration from about 5% w/w to 50% w/w; and ucuuba butter in a concentration from about 5% w/w to 50% w/w.

In this example, each of the aforementioned components possesses significant healing properties. Further to this example, aforementioned components employed together improve the effectiveness of the wound healing process as well as the treatment of scars.

In other embodiments, the topical pharmaceutical bases include one or more natural components, such as, for example buriti oil, bacaba oil, acai oil, ojon oil, murumuru butter, and/or tucuma oil, among others. In these embodiments, the concentration of each natural component within topical pharmaceutical bases is from about 1% w/w to 20% w/w, preferably about 5% w/w.

In some embodiments, the topical pharmaceutical bases include suitable active pharmaceutical ingredients (APIs), such as, for example antibiotic, antifungal, corticosteroids, non-steroidal anti-inflammatories, antibacterials, antivirals, and analgesics, among others. In these embodiments, aforementioned non-steroidal anti-inflammatory drugs include diclofenac, ketoprofen, ibuprofen, naproxen, and piroxicam, among others.

In other embodiments, topical pharmaceutical bases are employed within topical pharmaceutical compositions for scar treatments. In these embodiments, the topical pharmaceutical compositions include suitable APIs, such as, for example tamoxifem, metaxalone, and tranilast, among others.

Pracaxi Oil

Pracaxi oil is obtained from the seed oil of the *Pentaclethara macroloba* tree, or pracaxi tree. The pracaxi tree is a deciduous tree from the legumes family, growing in altitudes below about 600 meters in many parts of northern Brazil, Guyana, Trinidad, and parts of Central America, and may reach between about 8 and about 35 meters in height. Pracaxi trees may sometimes be found in wetlands, and are resistant to water logging.

Pracaxi seeds include from about 45% to 48% fat, about 27% to 28% protein, and about 12% to 14% carbohydrates (see Table 1). Pracaxi seed oil includes the highest known natural concentration of behenic acid (about 20%) in a vegetable fat, more than six times higher than in peanut oil, and also includes about 35% of oleic acid. In some cases, pracaxi seed oil may include greater percentages of the aforementioned behenic acid and oleic acid. The oleic acid and lauric acid, contained within pracaxi oil are effective vehicles for delivering drugs through the skin.

TABLE 1

General composition of pracaxi oil.

| Components | Composition % |
|---|---|
| Fat | 45-48 |
| Protein | 27-28 |
| Carbohydrates | 12-14 |

In an example, the fatty acid composition of the pracaxi oil is illustrated below in Table 2. Compositions vary depending on the region and conditions in which the pracaxi tree grows.

TABLE 2

Fatty acid composition of the pracaxi oil.

| Fatty Acids | Carbon Atoms | Composition % |
|---|---|---|
| Lauric | 12:00 | 1.30 |
| Myristic | 14:00 | 1.21 |
| Palmitic | 16:00 | 2.04 |
| Stearic | 18:00 | 2.14 |
| Oleic | 18:10 | 44.32 |
| Linoleic | 18:20 | 1.96 |
| Linolenic | 18:30 | 2.31 |
| Behenic | 22:00 | 9.67 |
| Lignoceric | 24:00 | 14.81 |

TABLE 3

Specifications of the pracaxi oil.

| Indicators | Reference Value |
|---|---|
| Texture | Solid below 18.5° C., liquid viscous texture above this temperature |
| Color | Translucent yellow, yellowish-white when solid |
| Odor | Almost odorless |
| Melting point | 18.5° C. |
| Refractive index (40° C.) | 1.4690 |
| Iodine value | 65-70 g I2/100 g |
| Saponification value | 170-180 mg KOH/g |
| Acid value | 3-5 mg KOH/g |
| Peroxide value | 5-10 mEQ/kg |
| Density (25°) | 0.917 g/cm$^3$ |

Pracaxi oil has been widely employed within pharmaceutical compositions because of its cosmetic, therapeutic, and medicinal properties. Pracaxi oil is rich in organic acids with antioxidant, antibacterial, antiviral, antiseptic, antifungal, anti-parasitic, and anti-hemorrhagic properties. Because pracaxi oil possesses many of the aforementioned properties, pracaxi oil can be suitable oil for helping in the treatment of wounds and scars.

Pracaxi oil has a high amount of solid matter, not fatty acids, which makes pracaxi oil solidifies in cooler temperatures. The solid matter has gentle moisturizing and high cellular renewal promoting properties. It includes vitamin E, and has essential fatty acids, which make pracaxi oil suitable for topical pharmaceutical compositions.

Andiroba Oil

Andiroba oil is extracted from the *Carapa guianensis* tree. Andiroba oil is rich in omega-3 fatty acid, which is fast absorbed into the skin balancing the production of chemicals that cause inflammation, thereby improving blood circulation, diminishing the swelling and reducing pain. Andiroba oil is also a rich source of essential fatty acids, including oleic, palmitic, myristic and linoleic acids, and includes non-fatty components, such as, for example triterpenes, tannins, and alkaloids, which are isolated as andirobina and carapina.

Andirobia has healing and insect repelling properties that are attributed to the presence of limonoids. Limonoids have been proven to possess antiviral, antifungal, antibacterial, anti-neoplastic, insecticide, and anti-inflammatory properties.

Andiroba oil is one of the most commonly sold medicinal oils in the Amazon. Mixed with honey and copaiba oil, andiroba oil is a very popular anti-inflammatory medication used to treat throat infections and influenza. Andiroba oil also strengthens and embellishes hair, and when used in soap andiroba oil acts as a remedy for acne. Due to andiroba oil's enhanced skin penetration, andiroba oil is often used in massages to relieve bruises, dislocations, arthritis and rheumatism, as well as to sooth the surface of the skin and to bleach superficial stains.

In an example, the fatty acid composition of the andiroba oil is illustrated below in Table 4.

TABLE 4

Fatty acid composition of the andiroba oil

| Fatty Acids | Carbon Atoms | Composition % |
|---|---|---|
| Myristic | 14:00 | 0.3300 |
| Palmitic | 16:00 | 28.0300 |
| Stearic | 18:00 | 8.6900 |
| Oleic | 18:10 | 49.0800 |
| Linoleic | 18:20 | 11.0300 |
| Linolenic | 18:30 | 1.3500 |
| Arachidic | 20:00 | 0.2200 |
| Behenic | 22:00 | 0.3400 |

Copaiba Balsam

Copaiba balsam is extracted from the bark of the *Copaifera officinalis Jacq.* tree, where copaiba balsam accumulates in cavities within the tree trunk. The chemical composition of the oil-resin of copaiba includes approximately 72 sesquiterpenes (hydrocarbons) and 28 diterpenes (carboxylic acids), and the oil is composed by about 50% of each of these terpenes. Diterpenes are attributed in the majority for therapeutic applications, a scientifically proven fact. Sesquiterpenes are partially responsible for the aroma of the oil-resin and also have antiulcer, antiviral, and anti-rhinovirus properties. Researchers have found that the oil-resin of copaiba exhibits anti-inflammatory effects; these anti-inflammatory effects may be higher than that found in pharmaceutical compositions comprising diclofenac sodium even by two folds.

The inhabitants of the Amazon employ copaiba balsam as a topical treatment for wound healing, to stop bleeding, skin sores and psoriasis, all types of pain, skin disorders and for inflammation. Copaiba balsam may also have diuretic, antibacterial, expectorant, disinfectant, and stimulant properties, being the highest known natural source of caryophyllene, a well-known plant chemical that has been documented strong anti-inflammatory effects, among other therapeutically effects. In the cosmetic industry, copaiba balsam is used as a component of fragrance in perfumes and in cosmetics, such as, for example soaps and creams, because of its antimicrobial, anti-inflammatory, and emollient properties.

Ucuuba Butter

Ucuuba butter is obtained from the seeds of the *Virola sebifera* tree. Ucuuba butter includes high concentrations of lauric, myrist and palmitic acids, as well as vitamins C and A. It also accounts for 70% concentration of trimyristin, a triglyceride of myristic acid that is an aromatic essential oil largely used by the cosmetic, pharmaceutical and food industries.

The inhabitants of the amazon have used ucuuba butter for the treatment of rheumatism, arthritis, colic, ulcers, and hemorrhoids. Amazonian fishers mix ucuuba butter with buriti oil, and spread all over their bodies; this mix helps to avoid sun burn and also protects the skin from dehydration. Also, some skin products produced employing ucuuba butter have shown anti-inflammatory, healing, and anti-septic properties. This butter may also aid in water retention in the skin, thereby helping to restore elasticity to the skin and improving mature skin appearance.

In an example, the fatty acid composition of the ucuuba butter is illustrated below in Table 5.

TABLE 5

Fatty acid composition of the ucuuba butter

| Fatty Acids | Carbon Atoms | Composition % |
|---|---|---|
| Lauric | 12:00 | 18.1700 |
| Myristic | 14:00 | 73.8400 |
| Palmitic | 16:00 | 8.0000 |

Administration

In some embodiments, the topical pharmaceutical bases are directly administered onto the affected area, in a dosage that varies according to the size or weight of the patient. In these embodiments, a single dose is enough to observe healing within the next 7 days after administration.

In some embodiments, the topical pharmaceutical bases are in a dosage form selected from the group consisting of: pharmaceutically acceptable liquids, creams, oils, lotions, ointments, gels, roll-on liquids, skin patches, sprays, glass bead dressings, and synthetic polymer dressings, among others.

In some embodiments, the topical pharmaceutical bases are applied manually with or without an applicator, such as, for example a dropper or pipette; an applicator, such as, for example a swab, brush, cloth, pad, roll-on device, and sponge, among others; or with any other applicator, such as, for example a solid support including paper, cardboard or a laminate material, including material with flocked, glued or otherwise fixed fibers, among others.

In some embodiments, topical pharmaceutical compositions including the topical pharmaceutical bases increase the residence time of APIs within a wound or scar, thereby improving the penetration of APIs into the affected area. In these embodiments, the topical pharmaceutical bases provide relatively uniform distribution of the APIs within the topical pharmaceutical compositions. Further to these embodiments, the topical pharmaceutical compositions release APIs slowly, thereby enhancing treatment effectiveness.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A topical pharmaceutical composition comprising a pharmaceutically effective amount of at least one active pharmaceutical ingredient, and a synergistically effective amount of about 5% w/w to about 50% w/w ucuuba butter, about 5% w/w to about 50% w/w copaiba balsam, about 5% w/w to about 50% w/w andiroba oil, and about 5% w/w to about 50% w/w pracaxi oil.

2. The topical pharmaceutical composition of claim 1 further comprising at least one natural component selected from the group consisting of buriti oil, bacaba oil, acai oil, ojon oil, murumuru butter, and tucuma oil.

3. The topical pharmaceutical composition of claim 1 further comprising at least one natural component selected from the group consisting of about 1% w/w to about 20% w/w buriti oil, about 1% w/w to about 20% w/w bacaba oil, about 1% w/w to about 20% w/w acai oil, about 1% w/w to about 20% w/w ojon oil, about 1% w/w to about 20% w/w murumuru butter, and about 1% w/w to about 20% w/w tucuma oil.

4. The topical pharmaceutical composition of claim 1 further comprising at least one natural component selected from the group consisting of about 5% w/w buriti oil, about 5% w/w bacaba oil, about 5% w/w acai oil, about 5% w/w ojon oil, about 5% w/w murumuru butter, and about 5% w/w tucuma oil.

* * * * *